United States Patent [19]

Ismach

[11] 4,103,684
[45] Aug. 1, 1978

[54] HYDRAULICALLY POWERED HYPODERMIC INJECTOR WITH ADAPTERS FOR REDUCING AND INCREASING FLUID INJECTION FORCE

[76] Inventor: Aaron Ismach, 200 Upper College Ter., Frederick, Md. 21701

[21] Appl. No.: 755,475

[22] Filed: Dec. 30, 1976

[51] Int. Cl.² ............................................. A61M 5/30
[52] U.S. Cl. ............................................. 128/173 H
[58] Field of Search ........... 128/173 H, 173 R, 218 F, 128/218 R, 218 A, 223; 124/16 R; 185/37

[56] References Cited

U.S. PATENT DOCUMENTS

| 2,472,116 | 6/1949 | Maynes | 128/218 F |
| 3,057,349 | 10/1962 | Ismach | 128/173 H |
| 3,353,537 | 11/1967 | Knox et al. | 128/173 H |

Primary Examiner—Robert W. Michell
Assistant Examiner—Henry J. Recla
Attorney, Agent, or Firm—Edward H. Loveman

[57] ABSTRACT

A hypodermic jet injection device has a reciprocatable piston for discharging fluid from a chamber. A reciprocatable hollow plunger connected to the piston is hydraulically retracted against a spring bias to compress a coil spring. The plunger is hydraulically released to cause discharge of the fluid with maximum initial force and minimum final force determined by characteristics of the spring. An adjustment knob may be rotated to determine precompression of the spring. A first adapter assembly quickly mountable and dismountable on the adjustment knob includes a shaft adjustably positioned axially inside the plunger to limit retraction of the plunger and compression of the spring so that the maximum initial force of fluid discharge is reduced. Another adapter assembly may be used in place of the first adapter assembly and is also quickly mountable and dismountable on the adjustment knob and includes a housing carrying another shaft insertable into the plunger to abut one end thereof. Another coil spring in the housing is axially compressible by the other shaft when the plunger is hydraulically retracted. Both springs are compressed so that the force of fluid discharged is increased when the retracted plunger is hydraulically released.

4 Claims, 8 Drawing Figures

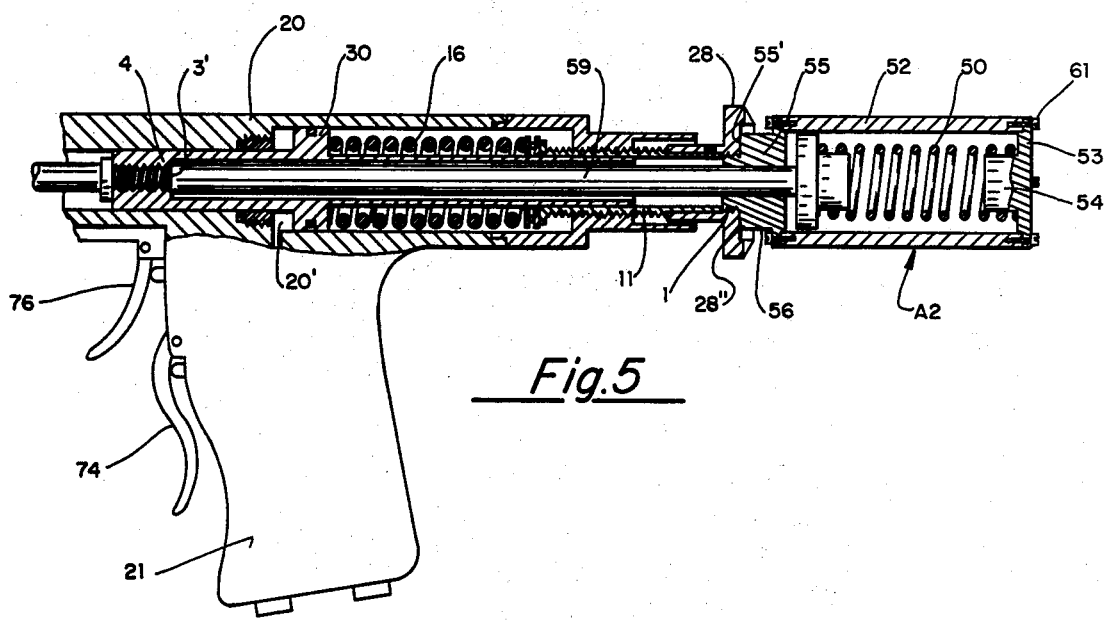
Fig.5
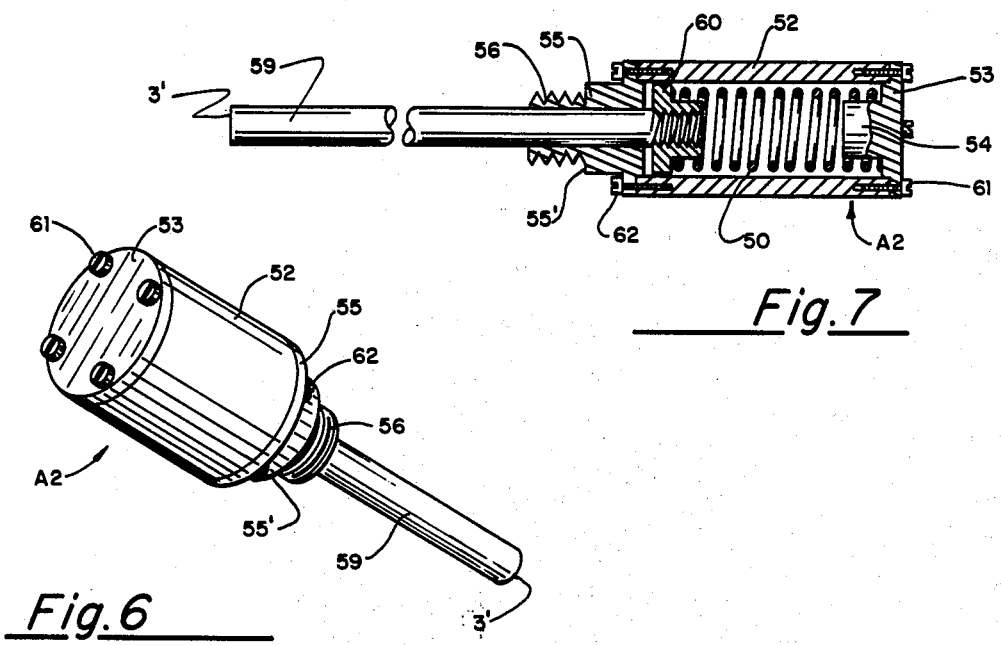
Fig.7
Fig.6

HYDRAULICALLY POWERED HYPODERMIC INJECTOR WITH ADAPTERS FOR REDUCING AND INCREASING FLUID INJECTION FORCE

This invention relates to the art of hypodermic jet injection apparatus and more particularly concerns adapters for reducing and intensifying the force of injection in such apparatus.

The invention is more particularly applicable to apparatus such as described in my prior U.S. Pat. No. 3,057,349, issued Oct. 9, 1962. This hypodermic jet injection apparatus is designed to administer either subcutaneous or intramuscular injections of aqueous drugs and vaccines. In this prior apparatus injections are administered with a fixed force. There are occasions when it is desirable to be able to vary the injection force, either reducing or increasing the force to inject a drug to a specific depth in body tissues. The jet injection apparatus described in U.S. Pat. No. 3,057,349 is not capable of such force variation.

The present invention provides means for extending the utility of the prior jet injector to new drugs and vaccines where the injection force provided by the prior jet injector is either too great or too low in magnitude to accomplish the desired medically specified effects or for use in animals and fowl. By the present invention if superficial or intradermal injections are desired, or if it is desired to inject chickens, an injection force reduction makes possible a mass injection program with all the inherent advantages of jet injection. If deep intermuscular injections are required to inject, for example, steers, an injection force intensification makes such a mass injection program possible. Deep injections are of growing importance for administering oil base drugs, such as repository antimalarial drugs. The prior jet injector described in U.S. Pat. No. 3,057,349 is not capable of efficiently administering such drugs, without the modifications and adapters provided by the present invention.

The injection force reducer adapter assembly permits shallow injections, such as intradermal smallpox vaccinations. Conventionally, shallow injections are limited to small doses, usually about 0.1 cc. If the prior jet injector is used without the present force reducer adapter, small doses of about 0.1 cc will be injected too deeply. Such excessively deep penetration is medically undesirable. When the force reducer adapter is installed, the injection force is reduced to limit injection force of a small quantity of fluid to the desired level in the skin. The present force reducer adapter is so arranged that injection force reduction is easily controllable in magnitude. Thus the present invention not only provides a lower than usual injection force, it also enables predetermined variation of the reduced injection force.

In the prior jet injector as described in U.S. Pat. No. 3,057,349 a rotatable spring setting knob determines the amount of precompression of a driving spring which determines the dosage that will be administered. The injection force is fixed for any given spring. At all times each injection regardless of dosage starts with the driving spring fully compressed. When the present adapter is installed, it provides an adjustable mechanical stop which prevents full compression of the driving spring. Thus the injection force is controllable reduced. The spring setting knob in cooperation with the adapter determines the injection force, while the setting of the adapter determines the dosage.

The prior hypodermic jet injector previously referred to above, has been found to provide inadequate injection force to administer intramuscular injections of certain oil-base drugs which are characterized by extremely high viscosity. Such a drug is the repositary type of antimalarial drug which requires deep penetration of a large quantity of the drug to be medically effective. If the penetration is not deep enough, painful sterile abscesses may develop. The present invention provides an injection force intensifier adapter which enables administration of a highly viscous, oil-base drug safely and effectively.

According to the invention, the injection force intensifier provides a supplemental spring which operates in parallel with the primary driving spring of the jet injector described in U.S. Pat. No. 3,057,349. Both springs are compressed when the injector is cocked. When the injector is fired, the resultant injection force is the sum of the driving forces provided by both springs.

It is therefore a principal object of the present invention to permit the operator of a known type of hypodermic jet injection apparatus or device to vary the injection force by installation of appropriate accessories or adapters.

Another object of the present invention is to provide adapters as just mentioned which are capable of quick, easy attachment and removal, without use of tools, from the injector apparatus, so that the apparatus can be used selectively with or without adapters.

A further object of the present invention is to provide an injector apparatus with adapters installed in such a way that sterility of the injector is maintained at all times.

These and other objects and many of the attendant advantages of this invention will be readily appreciated as the same becomes better understood by reference to the following detailed description when considered in connection with the accompanying drawings in which:

FIG. 5 is a longitudinal sectional view partially in side elevation of a portion of a hypodermic jet injector in which is installed an injection force intensifier adapter assembly according to the invention;

FIG. 6 is a perspective view on an enlarged scale of the injection force intensifier adapter per se;

FIG. 7 is an axial sectional view on a further enlarged scale of the injection force intensifier adapter.

Figure 1:
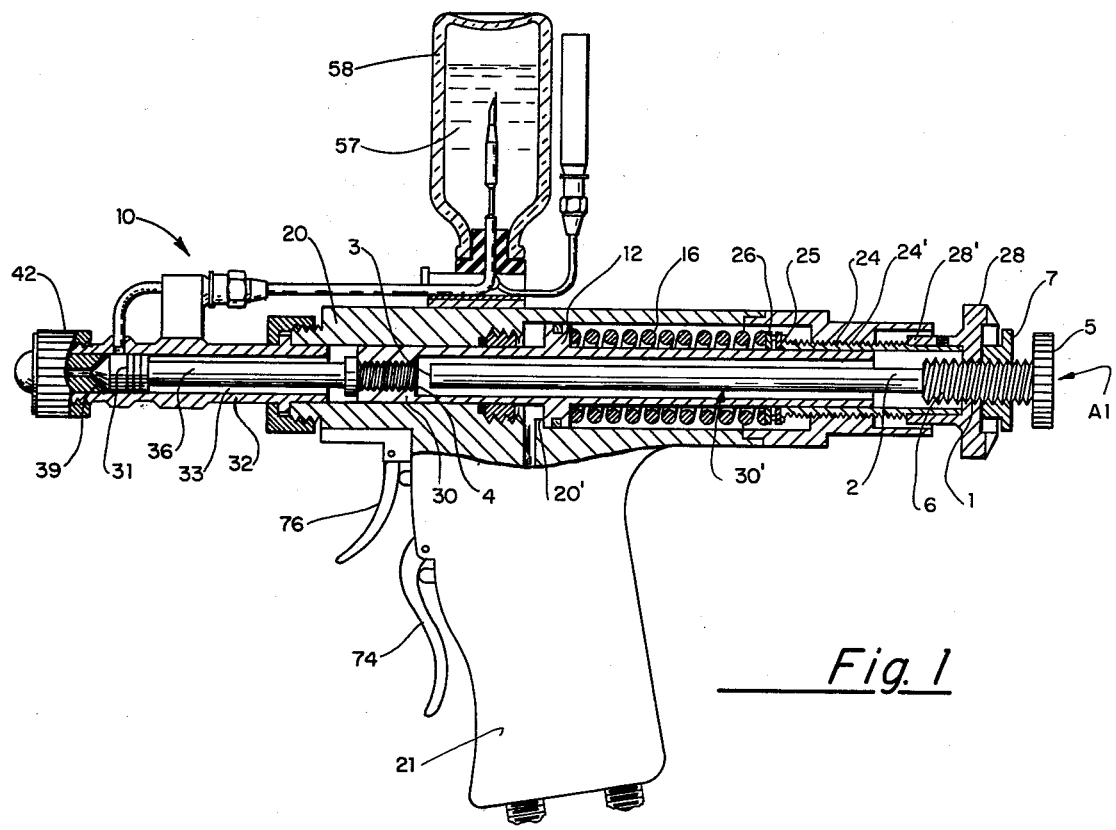
FIG. 1 is a longitudinal sectional view partially in side elevation of a hypodermic jet injector in which is installed an injection force reducer adapter assembly, according to the invention.

Referring now to the drawings wherein like reference characters designate like or corresponding parts with certain parts corresponding to those shown in prior U.S. Pat. No. 3,057,349 are identically numbered for convenience in reference thereto there is illustrated in FIG. 1, a hypodermic jet injector generally designated as reference numeral 10, having a barrel 20 integral with a hand grip 21. At the forward end of the injector 10 is a nozzle assembly 42. A bottle 58 containing a fluid drug or vaccine 57 to be administered is mounted on top of the barrel 20. Inside the barrel 20 is a hydraulic plunger 30 to which is secured a pump piston 36 which draws the fluid 57 into a chamber 39 between a nozzle assembly 42 and a piston head 31 when the piston 36 is retracted to the right, as viewed in FIG. 1. This occurs because hydraulic pressure acts on a flange 12 when a trigger 74 is manually retracted or cocked as described in the abovementioned U.S. Pat. No. 3,057,349. During the cocking action, a driving spring 16 in the barrel 20 is axially compressed by the annular flange 12 on the plunger 30, and is held in compressed position hydraulically. When firing trigger 76 is retracted hydraulic pressure on the plunger 30 is released and the spring 16 expands axially to the left as viewed in FIG. 1, to drive the plunger 30 and the piston 36 to the left, to effect forceful ejection of the fluid from the chamber 39. To the extent described, the jet injector 10 is identical to that described in the abovementioned U.S. Pat. No. 3,057,349.

Figure 3:
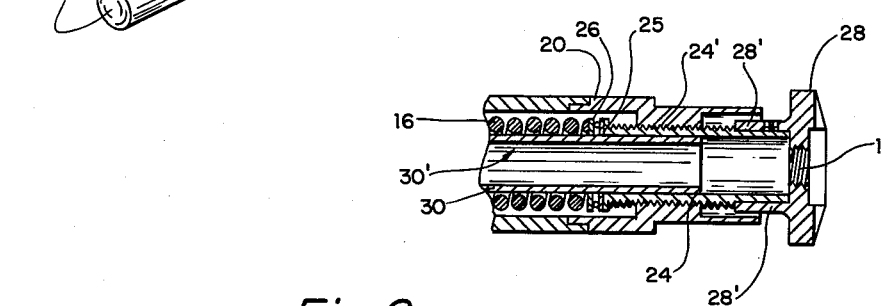
FIG. 3 is a perspective view of the injection force reducer adapter per se.
Figure 2:
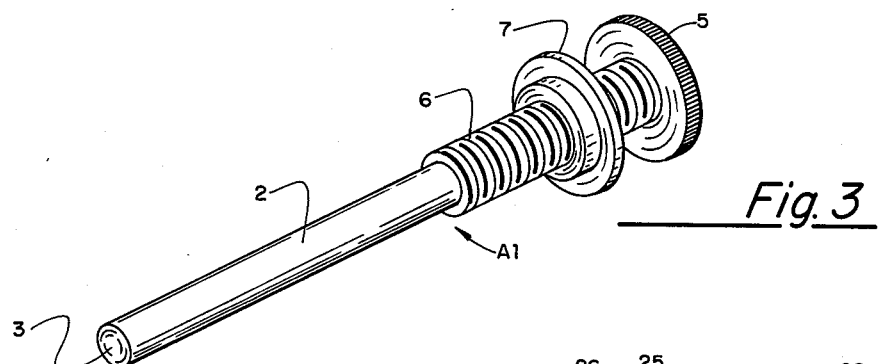
FIG. 2 is a fragmentary longitudinal sectional view of a portion of FIG. 1, with injection force reducer adapter removed.

An injection force reducer adapter assembly A1 is shown in FIG. 1 mounted in the rear end of the barrel 20. This assembly as clearly shown in FIGS. 1 and 2, comprises an elongated cylindrical shaft 2 having flat forward end 3 and a threaded rear end section 6. A manually turnable head 5 is integral with the shaft 2 at its rear end. On the threaded section 6 of the shaft 2 is a threaded locknut 7. At the rear end of the barrel 20 is a rotatable spring tension adjustment knob 28. This knob has an internal central bore 1 which according to this invention is threaded as clearly shown in FIGS. 1 and 3 to engage the threaded section 6 of the adapter shaft 2. The knob 28 has a sleeve 28' secured to a threaded screw 24 which has an end flange 25 abutting a bearing assembly 26 at the rear end of the spring 16. The screw 24 is threadedly engaged in an internally threaded section 24' of the barrel 20. When the adjustment knob 28 is turned the spring 16 is compressed under tension.

The flat end 3 of the shaft 2 is adjustably spaced from the annular end 4 of a bore 30' in the plunger 30. Adjustment is accomplished by rotating the shaft 2 by means of the head 5. After setting the shaft 2 in the desired position the locknut 7 is tightened to lock the shaft 2 in the set position in the knob 28.

In operation of the injector 10, without the adapter assembly A1, precompression of the spring 16 by rotational setting of the knob 28, determines the dosage that will be delivered. The injection force is determined by the physical properties of the spring 16 and is fixed for any particular spring. Thus, for example, if the spring 16 is precompressed to one-half its available travel axially, by means of the adjusting knob 28, it will be fully compressed the remaining half of its axial travel, when the injector is hydraulically loaded by hydraulic fluid acting on the plunger 30. During hydraulic loading of the plunger 30, the piston 36 moves rearwardly to the right as viewed in FIG. 1, to load the injector 10 with one half its maximum possible dose of vaccine or drug. At all times, each injection regardless of dose, starts with spring 16 fully compressed, when the adapter assembly A1 is not used. Thus ejection of the dose always starts with the same maximum force. The setting of knob 28 thus determines the dosage and final or minimum ejection force.

When the adapter assembly or accessory A1 is installed, the setting of the knob 28 will only determine the minimum injection force. The setting of shaft 2 will determine the dosage and maximum injection force. It will be noted that the face 3 of the shaft 2 acts as a mechanical stop on the internal face 4 of the bore 30' in the plunger 30, preventing complete compression of the spring 16. The spacing between the faces 3 and 4 determines the magnitude of the dose loaded into the injector 10 when the plunger 30 is retracted hydraulically. This spacing is preset by turning the head 5, causing the shaft 2 to travel axially along the thread 1 to engage with the thread 6.

Figure 4:
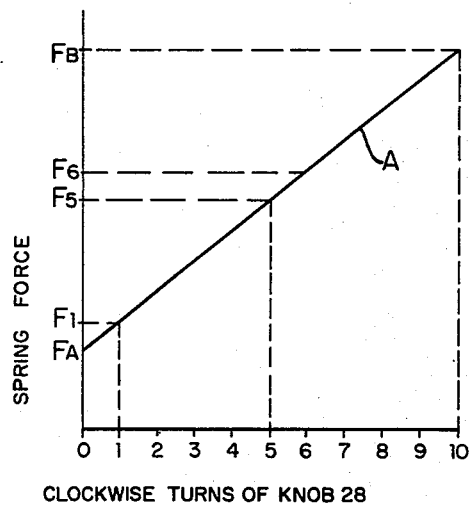
FIG. 4 is a graphic diagram used in explaining the operation of the injection force reducer adapter.

The operation of the injector 10 is illustrated graphically in FIG. 4. Here the spring tension of the spring 16 is plotted against clockwise rotational setting of the knob 28 to determine a curve A. For convenience, each clockwise turn of the knob 28 and the screw 24 can be made equal to a dose increment of 0.1 cc by suitable choice of the pitch of the thread 24', and diameter of the bore 33 in the forward barrel extension 32. In FIG. 4, ordinate $F_A$ represents the spring force when the screw 24 is fully retracted. This is the minimum possible spring force. Ordinate $F_B$ represents maximum spring force after ten clockwise rotations of the knob 28 and the screw 24 and after the spring 16 is fully compressed. In use of the injector 10 without adapter assembly A1, all injection start at injection force $F_B$ and terminate at a lower magnitude of force depending on the setting of the knob 28. Thus if a 1.0 cc injection is given, the final force is $F_4$. If 0.5 cc injection is given, the final force is $F_5$.

When the adapter assembly A1 is installed on the injector 10 as shown in FIG. 1, the dose to be injected will be determined by the position of the shaft 2. Suppose the spacing between the faces 3 and 4 is equivalent to 0.1 cc dose, and that the spring 16 is fully extended, with the knob 28 and the screw 24 retracted axially to maximum extent. Then hydraulic loading of the injector 10 will cause the spring 16 to compress to a force magnitude $F_1$. The injection force will have a maximum magnitude of $F_1$ at the start of injection and a minimum magnitude $F_A$ at the finish of injection. It will be apparent that the initial injection force of the injector has been reduced from previous maximum force $F_B$ (without the adapter assembly A1) to the low force $F_1$. Taking another example, suppose the knob 28 and the screw 24 have been rotated five turns, precompressing the spring 16 to exert force $F_5$ prior to installation of adapter assembly A1; and then the adapter assembly A1 is installed and the head 5 is turned to space the face 3 an axial distance equivalent to 0.1 cc dose. Now when the trigger 74 is retracted to cock the injector 10, the spring 16 will be further compressed hydraulically to a force magnitude $F_6$. It cannot be fully compressed because the face 3 of the shaft 2 then abuts the face 4 in the plunger 30. Then when the trigger 76 is retracted to fire the injector 10, the injection force magnitude will be $F_6$ at the start of injection and a lower force $F_5$ at the end of injection. Again it will be seen that the initial injection force has been reduced by use of the adapter assembly from $F_B$ to $F_6$. It will now be apparent that the initial injection force is limited by the position of the shaft 2, i.e. the limitation is a function of the position of the adapter adjusting head 5. Also it will be clear that the dose to be delivered is controlled by the setting of the adapter assembly A1 which determines the spacing between the faces 3 and 4.

In setting up the injector 10, it is preferable that the knob 28 and the screw 24 be adjusted to obtain predetermined initial compression of the spring 16. Then the adapter assembly A1 is installed with the face 3 of the shaft 2 contacting the plunger internal face 4. Then the shaft 2 is backed off by rotating the head 5 a measured amount, for example, by counting the turns of the head 5, to determine the dose to be drawn into the chamber 39. If desired a vernier type scale can be provided on the threaded portion 6 of the shaft so that direct readings of dosage can be made. It will be noted that installation of the adapter assembly A, does not affect the internal sterility of the dose reception chamber of cavity 39, nor does it affect the injection force at the end of dose discharge; however it does accomplish its primary object, which is to reduce, adjustably, the maximum initial dose injection force, and to transfer from the adjusting knob 28 to the adapter A1, the setting of dose to be discharged.

The force intensifier adapter assembly A2 shown in FIGS. 5, 6 and 7 will now be described. The maximum initial injection force $F_B$ indicated in FIG. 4 has been found to be inadequate to administer intramuscular injections of oil-base drugs which have very high viscosity. A typical drug of this kind is the repository type of antimalarial drug which requires deep penetration of a large volume of the drug to be effective. As pointed out above, if penetration is not deep enough painful abcesses may be developed. For administering such a drug safely and effectively, adapter assembly A1 is installed as an accessory on the basic injection device described in U.S. Pat. No. 3,057,349 referred to above. The force intensifier adapter assembly includes a coil spring 50 housed in a casing 52 having an end plate 53 formed with a central stud 54 on which one end of the spring 50 is engaged. The casing 52 has an apertured end flange 55 formed with a threaded nipple 56 which engages with the thread 1 formed in the knob 28; see FIGS. 2 and 5. A face 55' of the flange 55 abuts the shoulder 28" of the knob 28. A shaft 59 extends through the central aperture of the flange 55. A flanged nut 60 is screwed tightly on the threaded rear end of the shaft 58 and engages the front end of the spring 50. Screws 61, 62 hold the plate 53 and the flange 55 on opposite ends of the casing 52 to form a closed housing. The springs 50 and 16 are disposed in axial alignment when the adapter assembly A2 is installed as shown in FIG. 5. The front end face 3' of the shaft 59 abuts the inner face 4 of the plunger 30.

In operation of the injector device, it is hydraulically loaded by the retracting trigger 74 to cock the injector 10. The plunger 30 is forced axially rearwardly by compressing the spring 16. At the same time, the shaft 59 is forced rearwardly by the piston 30 to compress the spring 50, so that both springs 16 and 50 are loaded in parallel. When the injector 10 is fired by retracting the trigger 76, both springs 16 and 50 contribute to the injection force. The resulting force being the sum of the forces applied by both springs.

Figure 8:
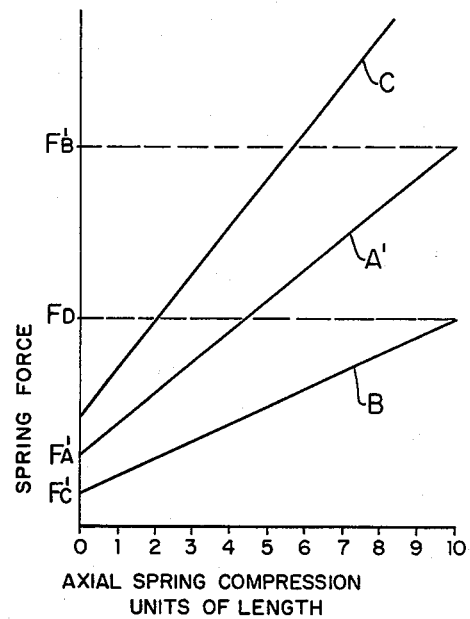
FIG. 8 is a graphic diagram used in explaining the operation of the injection force intensifier adapter.

FIG. 8 graphically illustrates the applied forces when the intensifier assembly A2 is used. The applied spring force is plotted against the axial spring compression in units of length. Curve A' represents the characteristics of the spring 16. The force $F'_A$ is the minimum force exerted by the spring 16 at maximum extension. The force $F'_B$ is the force exerted by the spring 16 at maximum compression. The curve B represents the characteristics of the spring 50. Force $F_C$ is the minimum force exerted at maximum spring extension, and the force $F_D$ is the maximum force exerted at maximum spring compression. Curve C is the resultant curve obtained by adding curves A' and B point by point. Each point on curve C is the resultant force exerted by both springs for any axial compression. The choice of spring characteristics of the spring 50 will determine curve B and consequently affect resulting curve C. In any case the spring 50 always operates to increase the injection force exerted over that exerted by the spring 16 along. It will be noted that when the knob 28 is turned any number of turns the spring 16 is compressed a certain axial distance. At the same time spring 50 is axially compressed the same distance because the end 3' of the shaft 59 remains stationary abutting the face 4 in the plunger 30 which is then held stationary at the abutment 20' in the barrel 20. It is of course essential that the hydraulic pressure exerted in cocking the injector 10 to retract the plunger 30, be sufficient in magnitude to compress the parallel combination of both of the springs 16 and 50.

Sterility of the chamber 39 containing the dose to be injected is not affected by the installation of the injection force increaser or intensifier A2. The injection force reducer and intensifier adapter assemblies A1, A2 are quickly installed, removed and interchanged without use of any tools. When desired the injector 10 can be used without either adapter assembly. But when either adapter assembly is installed it extends the range of minimum or maximum dose injection force exerted by the injector device.

It should be understood that the foregoing relates to only a limited number of preferred embodiments of the invention which have been by way of example only and that it is intended to cover all changes and modifications of the examples of the invention herein chosen for the purposes of the disclosure, which do not constitute departures from the spirit and scope of the invention.

The invention claimed is:

1. A hypodermic jet injection device comprising:
    a barrel having a chamber adjacent one end thereof for containing a quantity of fluid to be discharged;
    a reciprocatable piston in said chamber for discharging said fluid under pressure;
    a reciprocatable hollow plunger in said barrel secured to said piston;
    first trigger means arranged to initiate hydraulic retraction and retention of said plunger;
    second trigger means arranged to release hydraulic retention of said plunger;
    a coil spring in said barrel biasing said plunger toward said chamber and compressible by said plunger and operable when said plunger is released to drive said plunger and said piston forwardly toward said chamber a predetermined distance with a maximum initial driving force and a minimum final driving force to eject said fluid from said chamber;
    an adjustment knob means mounted on the other end of said barrel and abutting said coil spring for adjusting said minimum driving force at the forward end of travel of said piston;
    an adapter assembly means removably mountable on said adjustment knob and comprising means for varying said maximum initial driving force,
    said assembly comprising;
    a housing detachably mounted to said adjustment knob means;
    a shaft slidably mounted in said housing and extending from said housing coaxially said spring and said hollow plunger; said shaft terminating within said hollow plunger adjacent the point where said piston is secured to said plunger;

another spring in said housing axially aligned with said first named spring and operatively biasing said shaft towards said hollow plunger so that retraction of said shaft by said plunger, with respect to said adjustment knob means, simultaneously compresses both the first named spring and said other spring.

2. A hypodermic injection device as defined in claim 1, wherein said shaft is long enough axially so that an end of said shaft contacts an end of said plunger when said housing is securely mounted on said adjustment knob means, whereby both of said springs are compressed in parallel when said plunger is hydraulically retracted, so that said initial driving force is maximized.

3. A hypodermic injection device as defined in claim 2, further comprising a flanged member on the other end of said shaft engaging one end of said other spring in said housing opposite said flanged member, and a stud member carried by said housing engaging the other end of said spring to hold the same in axial alignment with said first named spring.

4. A hypodermic injection device as defined in claim 1, wherein said adjustment knob means has an internally threaded portion and said housing further includes an externally threaded end member engageable with said internally threaded portion of said adjustment knob for holding said adapter assembly and facilitating quick mounting and dismounting of said adapter assembly.

* * * * *